United States Patent
McLean

(10) Patent No.: US 6,174,917 B1
(45) Date of Patent: Jan. 16, 2001

(54) METHOD OF TREATING LIVER DISEASE AND LIKE INDICATIONS WITH VASODILATING AGENTS

(75) Inventor: Allan Joseph McLean, South Melbourne (AU)

(73) Assignee: Pharmacy and Therapeutic Advisory Consultancy Ltd., London (GB)

( * ) Notice: Under 35 U.S.C. 154(b), the term of this patent shall be extended for 0 days.

(21) Appl. No.: 09/213,278

(22) Filed: Dec. 17, 1998

Related U.S. Application Data

(63) Continuation-in-part of application No. 08/667,147, filed on Jun. 20, 1996, now Pat. No. 5,854,233, which is a continuation-in-part of application No. PCT/AU94/00525, filed on Sep. 5, 1994, and a continuation-in-part of application No. 08/612,286, filed on Mar. 7, 1996, now abandoned.

(30) Foreign Application Priority Data

Sep. 8, 1993 (AU) .................................. PM 1104

(51) Int. Cl.$^7$ ...................................... A61K 31/21
(52) U.S. Cl. .......................... 514/509; 514/211; 514/213; 514/259; 514/307; 514/356; 514/398; 514/401
(58) Field of Search ................................... 514/211, 213, 514/259, 307, 356, 398, 401, 509

(56) References Cited

U.S. PATENT DOCUMENTS

| | | | |
|---|---|---|---|
| 4,902,684 | 2/1990 | Floyd et al. | 514/211 |
| 5,569,678 | 10/1996 | Lee | 514/654 |

FOREIGN PATENT DOCUMENTS

| | | |
|---|---|---|
| 44849/68 | 10/1968 | (AU) . |
| 16326/92 | 5/1992 | (AU) . |
| WO 92/04008 | 3/1992 | (WO) . |
| WO 95/07080 | 3/1995 | (WO) . |

OTHER PUBLICATIONS

Li et al. "Significance of serum procollagen III peptide in reflecting . . . " Medline abs. 91199696, 1990*

Sugano et al. "Chronic splanchnic hemodynamic effects . . . " Pascal No. 97–0238412, 1997.*

Temkin "High–dose monotherapy and combination therapy . . . " Embase 1989060780, 1989.*

Marteau et al., "Effect of Vasodilators on Hepatic Microcirculation: A Study of the Inhibition of Norepinephrine–Induced Vasoconstriction in the Isolated Perfused Rat Live", Hepatology, vol. 8, No. 2, 1988, pp. 228–231, XP000673345.

Marteau et al., Effect of Vasodilators on Hepatic Microcirculation in Cirrhosis: A Study in the Isolated Perfused Rat Liver, Hepatology, vol. 9, No. 6, pp. 820–823, XP000673346.

Hierlinger, "Chronic Verapamil Administration Improves Liver Function and Diffusional Exchange in a Rat Model of Liver of Liver Cirrhosis", J. Hepatol., No. Suppl. 2, 1985, pp. S253, XP0002030787.

Romano et al., "Alterazione degli enzimi epatici in corso di terapia con diltiazem", g. Ital. Cardiol., vol. 17, No. 2, 1987, pp. 149–150, XP000673314.

Navasa et al., "Effects of Verapamil on Hepatic and Systemic Hemodynamics and Liver Function in Patients with Cirrhosis and Portal Hypertension", Hepatology, vol. 8, No. 4, 1988, pp. 850–854, XP000673312.

Merkel et al., "Lack of effect of verapamil and isosorbide dinitrate on the hepatic clearance of indocyanine green in cirrhosis", Br. J. Clin. Pharmacol., vol. 30, No. 2, 1990, pp. 221–228, XP000673273.

Gasic et al., "Comparative effects of verapamil, tiapamil, diltiazem and nifedipine on systemic and splanchnic hemodynamics in man", Int. J. Clin. Pharmacol. Ther. Toxicol., vol. 25, No. 9, 1987, pp. 498–503, XP000673344.

MacMathuna et al., "Vasopressin–nifedipine: a favourable haemodynamic interaction in cirrhosis and portal hypertension", Eur. J. Gastroenterol. Hepatol., vol. 5, No. 10, 1993, pp. 853–857, XP000673271.

Extract from The Merck Manual of Diagnosis and Therapy, 16$^{th}$ Edition; Merck Research Laboratoriesl; Ch. 286, 1989, pp. 2670–2671.

Hubert J. Stein et al., "Effect of Verapamil on Hepatic Ischemia/Reperfusion Injury", The American Journal of Surgery, vol. 165, Jan. 1993, pp. 96–100.

Decai Liang et al., "Protective Effects of the Calcium Antagonists Diltiazem and TA3090 Against Hepatic Injury Due to Hypoxia", Biochemical Pharmacology, vol. 43, No. 4, pp. 913–915, 1992.

David Le Couteur et al., "Aging and the Response of the Isolated Perfused Rat Liver to Vasoactive Drugs", Biochemical Pharmacology, vol. 43, No. 4, pp. 913–915, 1992.

Nobuyuki Ogawa et al., "comparison of KRN2391 with Nicorandil and Nifedipine on Canine Coronary Blood Flow: Antagonims by Glibenclamide", Journal of Cardiovascular Pharmacology, pp. 11–17, 1992.

Stephen Cheng, et al., "Verapamil Improves Rat Hepatic Preservation with UW Solution", Journal of Surgical Research 50, pp. 560–564, 1991.

(List continued on next page.)

Primary Examiner—Ceila Chang
(74) Attorney, Agent, or Firm—McDermott, Will & Emery

(57) ABSTRACT

Liver diseases, such as cirrhosis of the liver, toxic and medicamentary liver damage, a liver-parenchymic disorder or hepatitis, are treated by administering to a human or animal subject in need thereof a therapeutically active or prophylactically effective low dose amount of a vasodilating agent which selectively increases the supply of oxygenated blood to the liver by increasing hepatic arterial inflow; Suitable vasodilating agents include calcium blockers, such as a benzothiazepine derivative, nifedipine, felodipine or verapamil.

6 Claims, 12 Drawing Sheets

OTHER PUBLICATIONS

William G. Reiss et al., "The Effects of Oral Nifedipine on Hepatic Blood Flow in Humans", Clinical Pharmacology and Therapeutics, vol. 50, pp. 379–384, Oct. 1991.

Jiri Heller et al., "The effect of two difference calcium antagonist on the glomerular haemodynamics in the dog", European Journal of Physiology (Berlin), vol. 415, No. 6, pp. 751–755, 1990.

Denis B. Buxton, "Potentiation of the glycogenolytic and haemodynamic actions of adenosine in the perfused rat liver by verapamil", European Journal of Pharmacology, 146, pp. 121–127, 1988.

J. Reichen et al., "Verapamil Favorably Influences Hepatic Microvascular Exchange and Function in Rats with Cirrhosis of the Liver", The American Society for Clinical Investigation, Inc., vol. 78, Aug. 1986, pp. 448–455.

P.A. Meredith et al., "Verapamil Pharmacokeinetics and Apparent Hepatic and Renal Blood Flow", British Journal of Clinical Pharmacology, vol. 20, No. 2, 1985, pp. 101–106.

G. Johnsson et al., "Haemodynamic Effects of a New Vasodilator Drug, Felodipine, in Healthy Subjects", European Journal of clinical Pharmacology, 1983, pp. 49–53.

Patent Abstracts of Japan JP 5–59028, Yoshiaki Oshida, "Benzothiazepine Derivative, its Salt and Medicine Composition Containing the Same", Mar. 9, 1993.

Patent Abstracts of Japan JP 56–68619, Yamanouchi Seiyaku, "Nifedipine—Containing Solid Composition", Jun. 9, 1981.

* cited by examiner

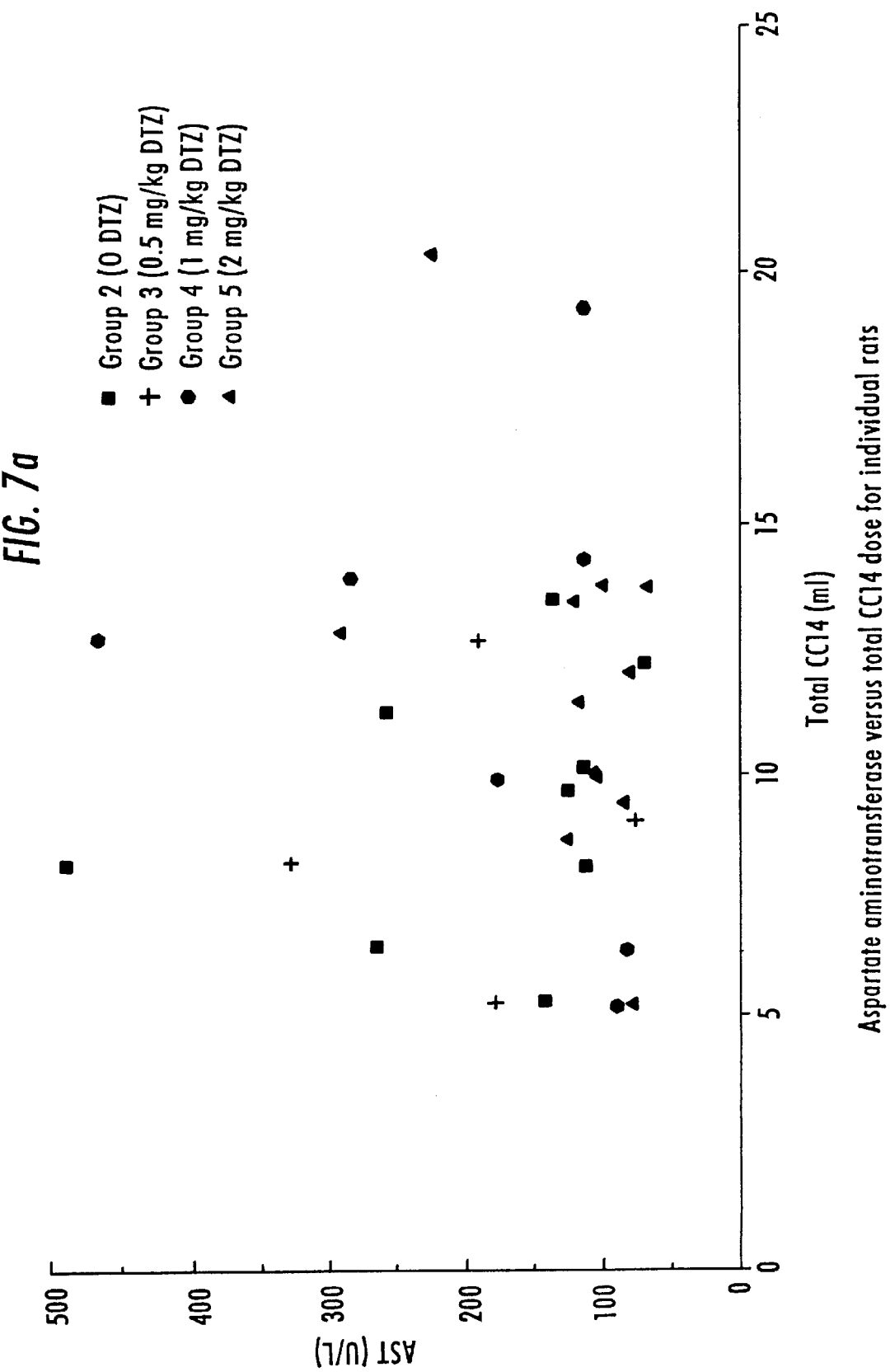

METHOD OF TREATING LIVER DISEASE AND LIKE INDICATIONS WITH VASODILATING AGENTS

This is a continuation-in-part of U.S. 08/667147 filed Jan. 20, 1996, now U.S. Pat. No. 5,854,233, which is a continuation-in-part of PCT International application Ser. No. PCT/AU94/00525, filed Sep. 5, 1994, and a continuation-in-part of U.S. patent application Ser. No. 08/612,286, filed Mar. 7, 1996.

TECHNICAL FIELD

The present invention relates to a method for the treatment of liver disease. The invention also relates to compositions suitable for the use in the treatment of liver disease.

Diltiazem is the generic name given to the active component of a composition that is primarily used for the treatment of heart disease. Specifically it is known as 3-acetoxy-5-(2-(dimethylaminoethyl)-2,3-dihydro-2-(4-methoxy phenyl)-1,5-benzothiazepine4)5H-one. This compound is the active ingredient in the heart treatment drug Cardizem. Cardizem has particular efficacy in the treatment of ischaemic heart disease including angina pectoris and hypertension.

Diltiazem is a member of a broad class of benzothiazepine derivatives that are the subject of Australian Patent 426146. The class of compounds are referred to in that specification as having particular utility as anti-depressants, tranquilizers and coronary vasodilators.

Diltiazem primarily acts as a calcium channel antagonist (a calcium blocker), calcium being involved in several biological processes in the human body including vasoconstriction and vasodilation. Calcium blockers interfere with the transport of calcium through the cell membrane, thus reducing the contraction of vascular smooth muscle and causing the arteries to dilate. The discovery of calcium blockers constituted a major advance in cardiovascular treatment Diltiazem contributed significantly to this advance. Generally, during cardiovascular treatment using Diltiazem, a patient in need thereof is administered the drug in doses of from 180 mg to 360 mg per day.

The liver is a large gland situated in the upper part of the abdomen on the right side. Its domed upper surface fits closely against the inferior surface of the right diaphragm. It has a double blood supply from the hepatic artery (oxygenated arterial blood) and the portal vein (deoxygenated venous blood carrying substances absorbed from the stomach, small intestine and large intestine). It comprises thousands of minute lobules (lobuli hepatis), the functional units of the liver. Its manifold functions include the storage and filtration of blood, the secretion of bile, the excretion of bilirubin and other substances formed elsewhere in the body, and numerous metabolic functions, including the conversion of sugars into glycogen, which it stores. It is essential to life and accordingly liver disfunction is debilitating and life threatening.

Prior art treatments of liver disease have included use of a number of drugs. For example, choline has been administered as an adjunct to the dietary treatment of fatty acid infiltration and early cirrhosis of the liver. Methionine has a lipotropic action similar to choline. It has also been used as an adjunct in the treatment of liver diseases in patients unable to take an adequate diet, though there is evidence that in cases of severe liver damage large doses of methionine may aggravate the toxaemia. Litrison is a composition of methionine, choline, vitamins of the B complex and Vitamin E. It has been used for the treatment of hepatic parenchymal degenerative changes and to maintain the function of the liver. Neurogem is a composition of high potency essential Vitamin B-complex and Vitamin C which has been used for supplementary or maintenance therapy. Finally, Ripason is a protein-free total extract from livers of healthy animals. It has been used to treat chronic hepatitis, cirrhosis, medicamentous liver damage and liver parenchyma disorders.

The treatment of liver disease, however, has been an ongoing difficulty in the prior art and none of the drugs used have proved to be particularly effective. In particular, none of these agents reverses the relative hypoxia, or oxygen lack, which appears to contribute to the pathology and progression of chronic liver disease. Accordingly, liver disease continues to be a life-threatening disease and ultimately may require surgery or even transplants in some cases.

Accordingly, it is an object of the present invention to overcome, or at least alleviate, one of more of the difficulties or deficiencies related to the prior art.

Accordingly, in a first aspect of the present invention, there is provided a method for the treatment of liver disease selected from the group consisting of cirrhosis of the liver, toxic and medicamentary liver damage, a liver-parenchymic disorder or hepatitis, which method includes administering orally to a human or animal subject in need thereof a vasodilating agent at a dose less than the oral dose required to produce a significant effect on the heart or peripheral circulation whereby said vasodilating agent selectively increases the supply of oxygenated blood to the liver by increasing hepatic arterial inflow.

The vasodilating agent may include a calcium blocker, e.g. a thiazepine derivative, preferably a benzothiazepine derivative, nifedipine, felodipine, verapamil or other vasodilator. Other vasodilators may be used indirectly.

The method of treatment may be utilised in the treatment of various diseases of the liver such as cirrhosis of a liver, toxic and medicamentary liver damage or liver parenchymic disorders and related diseases such as hepatitis including chronic active hepatitis.

The method of treatment may be directional in that significantly lower doses may be used then are normally administered in the treatment of heart disease or like indications.

BRIEF DESCRIPTION OF THE DRAWINGS

Reference is now made to the drawings which accompany the application wherein:

FIGS. 7a and 7b are plots of AST and ALT enzyme release vs. Total Body load of $CCl_4$ of data from Table 3.

Figure 1:
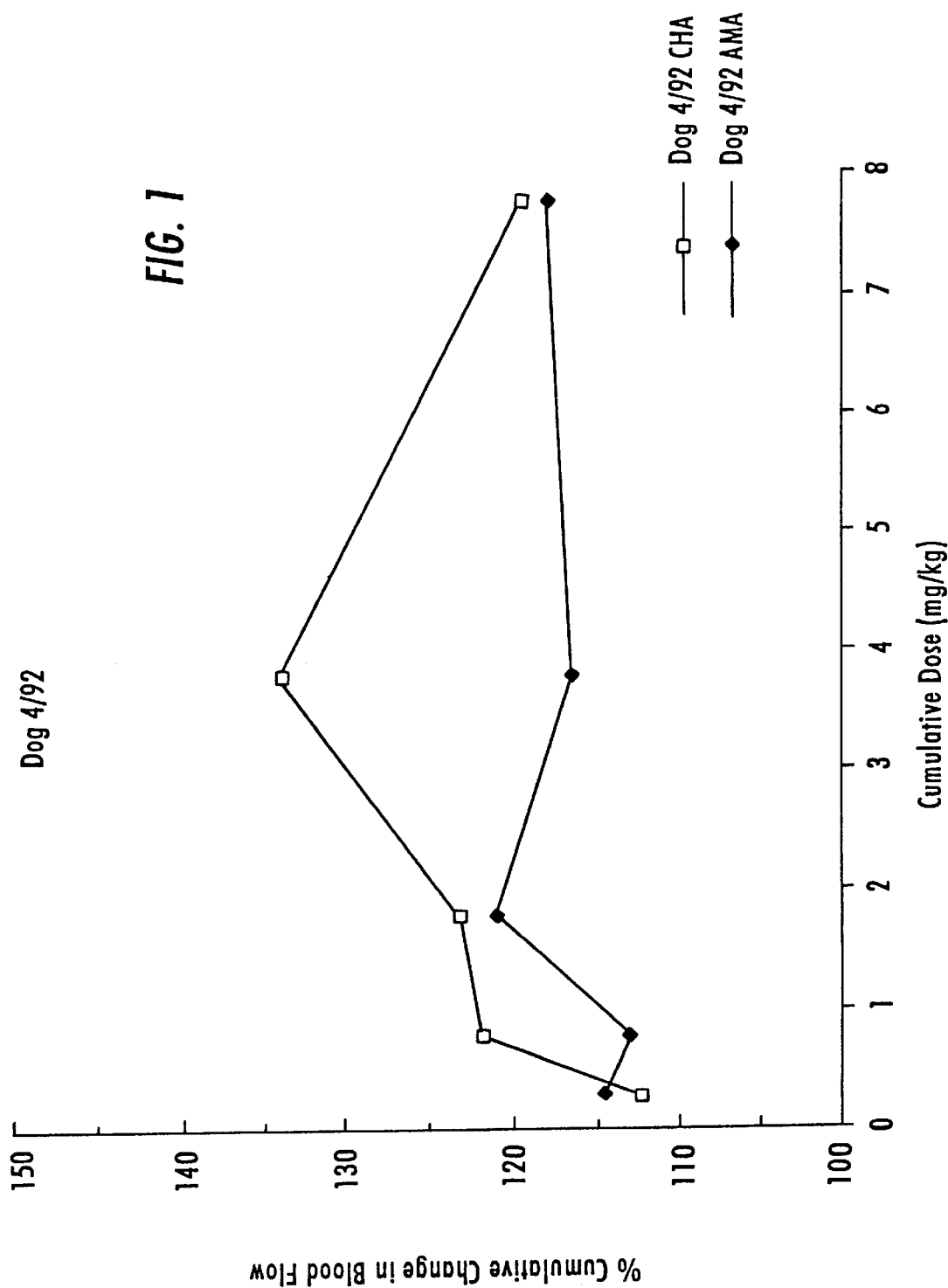
FIGS. 1, 2, 3, 4, and 5 are graphs of the results shown in Tables 2a and b.
Figure 2:
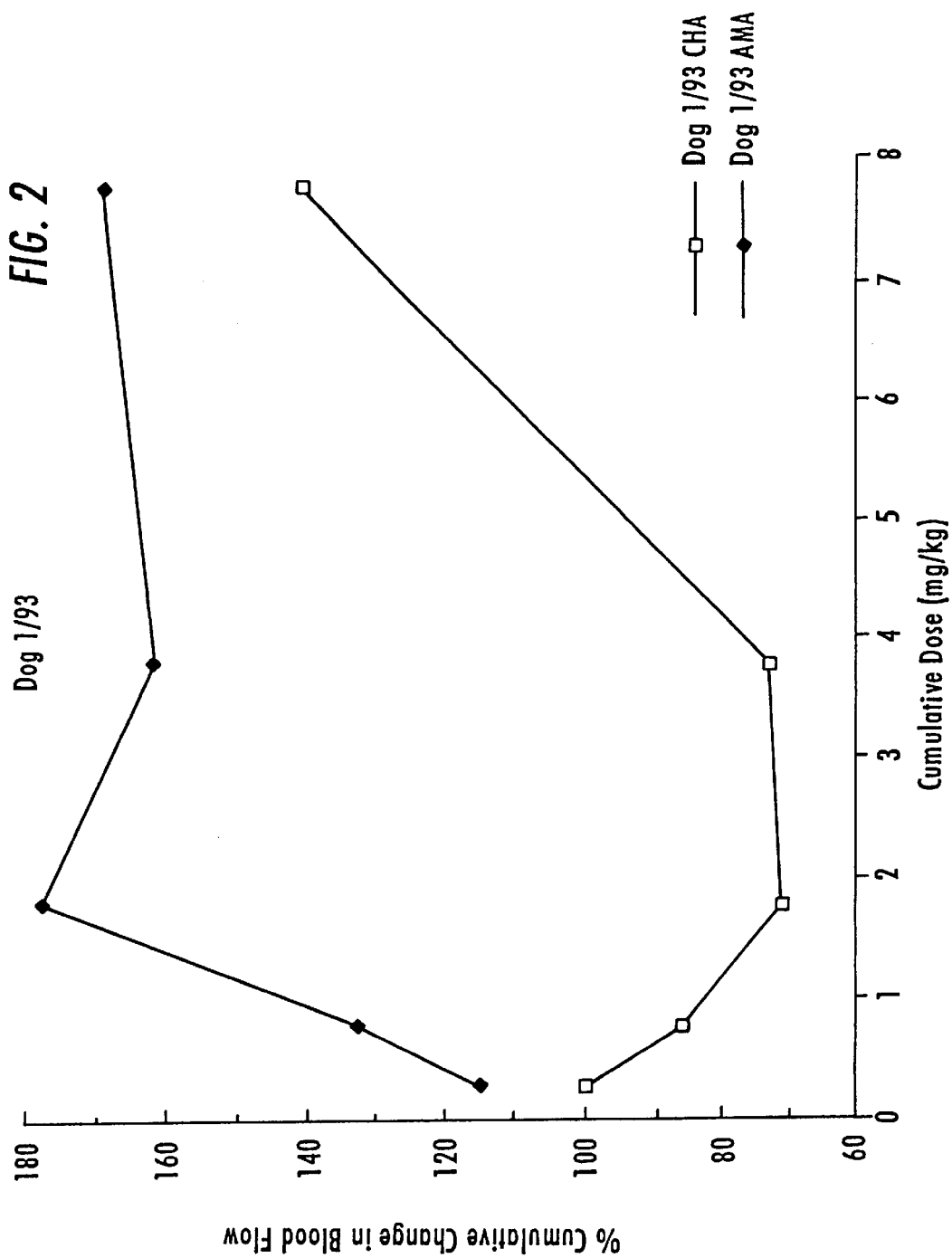
Figure 3:
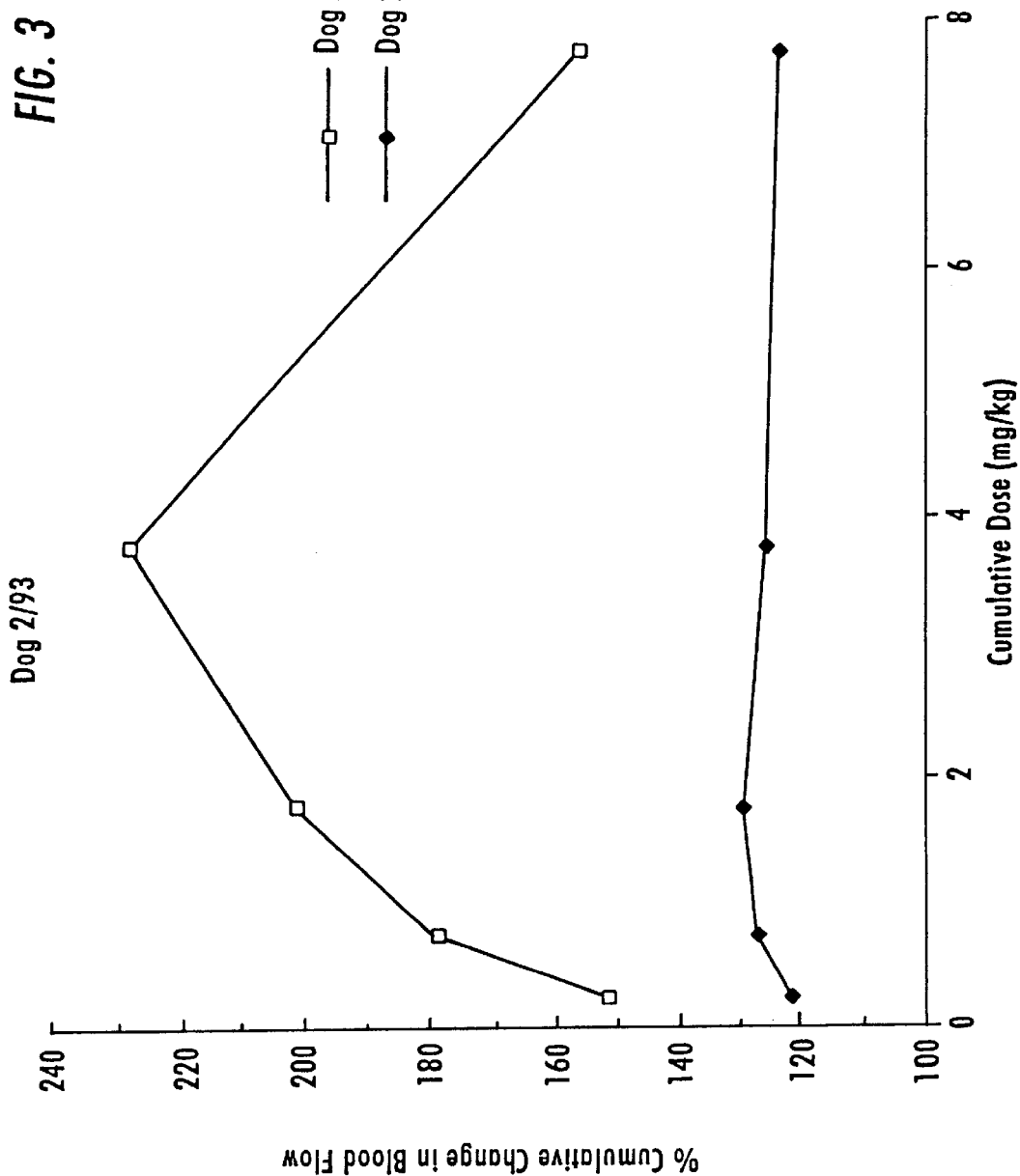
Figure 4:
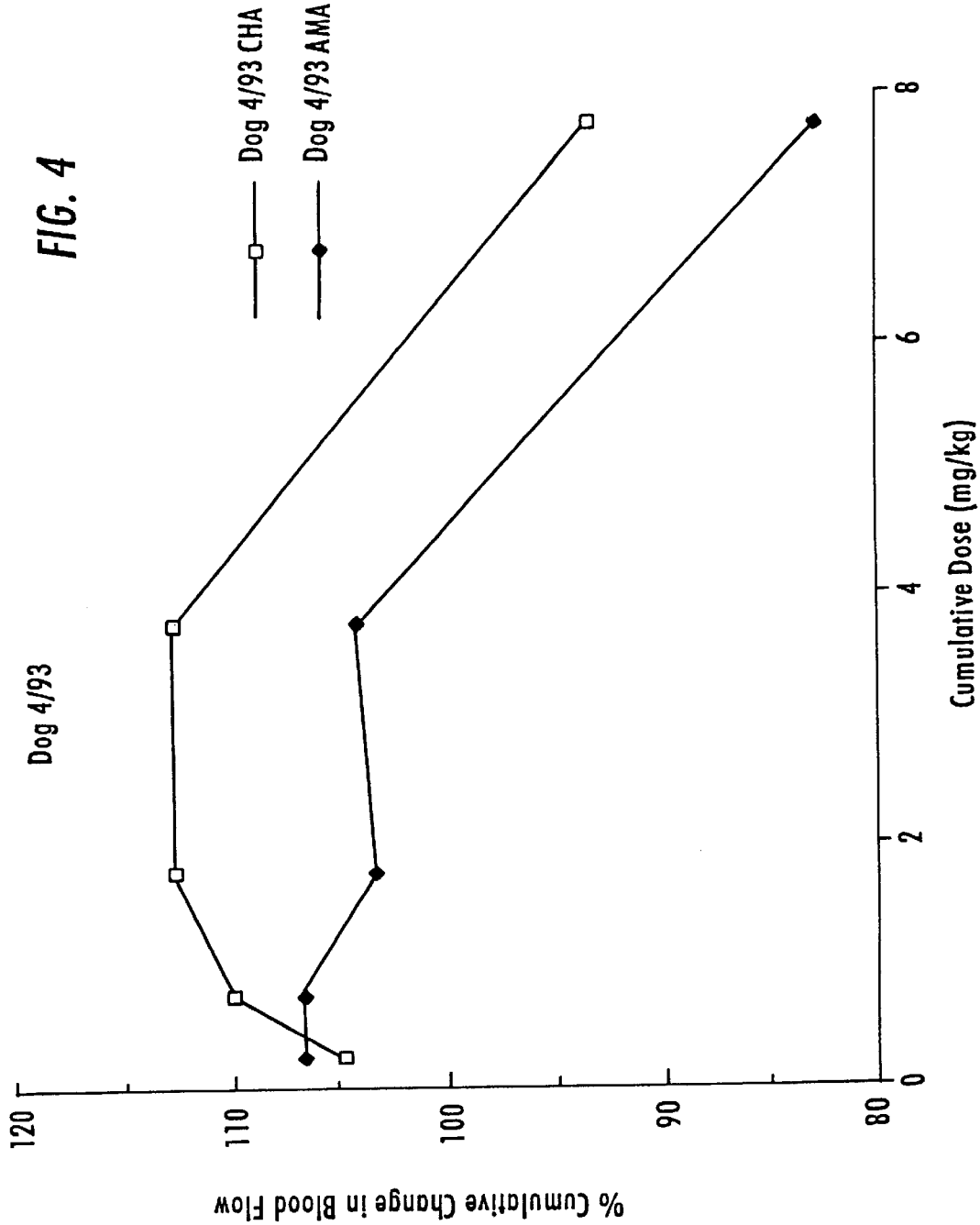
Figure 5:
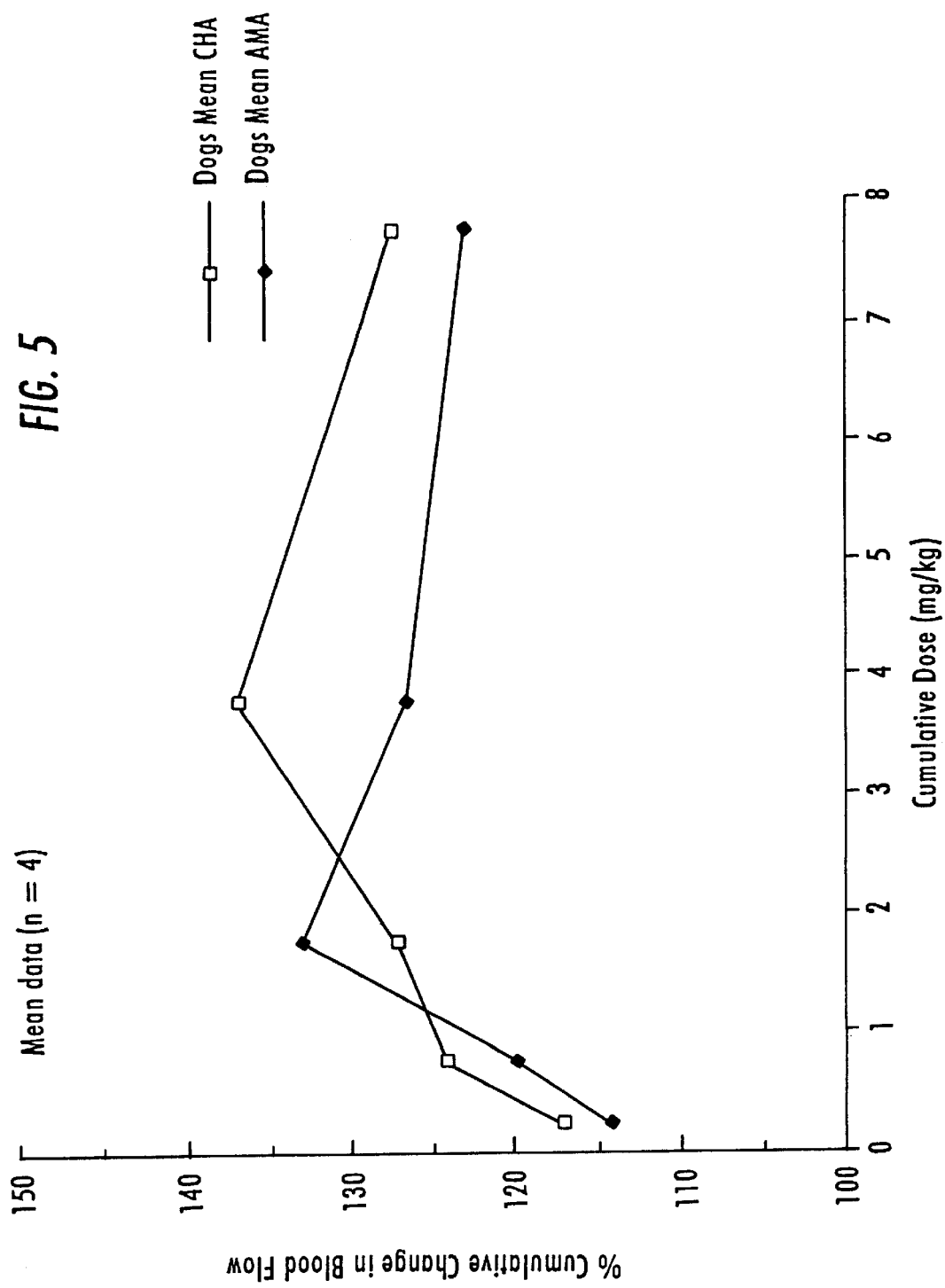

Whilst we do not wish to be restricted by theory, it is believed that the class of vasodilating agents known as calcium blockers are effective in the treatment of liver disease as they are selectively able to increase the oxygen content to the liver. In particular, it is believed that calcium blockers are effective in the treatment of liver disease as they are, when administered orally at doses less than required to effect the heart or peripheral circulation, selectively able to dilate the hepatic artery. At doses generally used in cardiovascular treatment the effect on the peripheral circulation reduces blood pressure and the effect of selectively increasing hepatic arterial blood flow is lost. An increase in oxygen level may alleviate the progress of liver disease, since liver performance generally increases with an increase in the oxygen concentration. Common liver diseases, such as chronic hepatitis or cirrhosis of the liver, share as a pathological feature a low concentration of oxygen in the liver.

The vasodilators used in accordance with the method of the invention may produce vasodilation by any of a wide range of mechanisms.

One suitable class of vasodilators are the adrenergic neurone blockers which interfere with transmission in the nerve. Several nerve types may be acted upon to produce vasodilation depending on the pharmacological category of the agent. The vasodilators in this class include debrisoquine which is available under the trade name DECINAX.

Further classes of vasodilators act on pharmacological receptors on the smooth muscle membrane. These include presynaptic receptor blockers and vasodilators which reduce the amount of chemical messenger in the synaptic vesicles which provide the point of contact with the smooth muscle. An example of the former type is clonidine available under the trade name CATAPRES and an example of the latter type is guanethidine available under the trade name ISMELIN.

One specific class of vasodilators act on catecholamine transmitters and are termed alpha-adrenergic blocking agents. Example of this type of vasodilator include prazosin available under the trade name MINIPRESS, lebetaiol available under the trade name TRANDATE, doxazocin available under the trade name CARDURAN, phenoxybenzamine available under the trade name DIBENYLINE, phentolamine available under the trade name REGITINE, betahistine available under the trade name SERC, ergotamine available under the trade name CAFERGOT and Sumatripton available under the trade name IMMIGRAN.

There are several other receptor types present on the smooth muscle cell which mediate contractions and Vasodilation results when actuation of these receptors is interferred with Renin receptors and angiotensin II receptors mediate such contractions, and agents which block these processes indirectly or directly are Vasodilators. ACE inhibitors and Angiotensin II receptor antagonists are two categories which are known and have commercially marketed representatives. Angiotensin II receptor antagonists include ibesartan (KARVEA, AVAPRO). The ACE Inhibitors include quinapril (ACCUPRIL, ASIG) captopril (ACENORM, CAPACE, DBL CAPTOPRIL, ENZACE, SBA CAPTOPRIL WL CAPTOPRIL), enalapril (AMPRACE, RENITEC), perindopril (COVERSYL), trandolapril (GOPTEN, ODRIK), cilazapril (INHIBACE) fosinopril (MONOPRIL), lisinopril (PRINIVIL, ZESTRIL) and ramipril (RAMACE, TRITACE).

There are other nerve processes which mediate contraction-these are the purinergic and neuropeptide Y transmitter and receptor systems and vasodilators which act on these nerve processes may be used in accordance with the invention.

Similarly there is a range of receptor types which may be targeted to provide the vasodilator effect. These include α, adrenergic (including α1A, α1B and α1C), α2 adrenergic (including α2A, α2B and α2C), Neuropeptide Y (including $Y_1$, and $Y_2$) and Purinergic (including $P_{2x1}$, $P_{2x2}$, $P_{2x3}$, $P_{2x4}$, $P_{2x5}$, $P_{2x6}$, $P_{2x7}$).

A further major class of vasodilators are those which act directly in the smooth muscle membrane. They include hydrallazine (ALPHAPRESS), verapamil (ANPEC), diltiazem, felodipine (FELDOURER), minoxidil (LONITEN), amlodipine (NORVASC), glyceryl trinitrate (ANGININE, IMDUR), isosorbide mononitrate (DURIDE), nicorandil (IKOREL), dipyridamole (PERSANTIN), multiple actives (PROFLO), alprostadil (PROSTIN VR), oxpentifylline (TRENTAL), hydroxyethyl rutosides & tartrazine (VAREMOID), adenosine (ADENOSCAN) and nimodipine (NIMOTOP).

Benzothiazepine derivative include compounds of the formula:

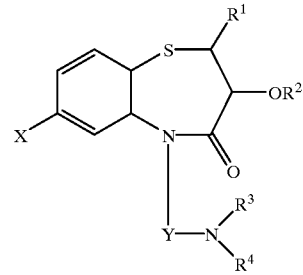

wherein $R^1$ is a phenyl group substituted or not with 1 to 3 lower alkyl groups, lower alkoxy groups or halogen atoms, $R^2$ is a hydrogen atom or a lower alkanoyl group, $R^3$ and $R^4$ are each a lower alkyl group and may be the same or different, X is a hydrogen atom or a halogen atom and Y is an alkylene group of 2 or 3 carbon atoms. or its non-toxic acid-addition salt.

Preferably $R^1$ is 4-lower alkoxyphenyl, $R^2$ is lower alkanoyl, $R^3$ and $R^4$ are each lower alkyl, X is hydrogen and Y is ethylene. More preferably $R^1$ is 4-methoxyphenyl, $R^2$ is acetyl and $R^3$ and $R^4$ are each methyl. Still more preferably, the benzothiazepine derivative is 3-acetoxy-5-(2-(dimethylaminoethyl)-2,3-dihydro-2-(4-methoxyphenyl)-1,5-benzothiazepine-4)5H-one.

The benzothiazepine derivative may be converted into its acid-addition salts by treatment with an organic or inorganic acid (e.g acetic acid, oxalic acid, malonic acid, tartaric acid, malic acid, citric acid, lactic acid, gluconic acid, aspartic acid, hydrochloric acid, hydrobromic acid, sulfuric acid, nitric acid, ID perchloric acid, etc.) in a suitable solvent (e.g. water, methanol, ethanol, etc.). It has been found that the use of such benzothiazepine derivatives is effective in increasing the hepatic arterial blood flow to the liver. Such benzothiazepine derivatives may be effective in the treatment of liver disease in significantly lower doses than is normally administered in the treatment of heart diseases. Significantly lower mean doses which will have no significant effect on heart or peripheral circulation.

In a further preferred aspect of the present invention there is provided a method of treating liver disease which method includes administering to a patient in need thereof a low dose, e.g., approximately 2.5 mg to 100 mg per day, more preferably approximately 2.5 mg to 60 mg/day, and even more preferably 10 mg to 60 mg/day of a vasodilating agent. Experimental studies in rats to date have indicated effective doses of approximately 1.0 to 2.0 mg/kg/day. However, it is common for human doses to be lower than for animals including rodents. A dose of approximately 2.5 mg to 30 mg for the most severe grades, preferably 10 mg to 30 mg, per day may be used for patients with various higher grades of liver disease. A dosage of approximately 30 mg to 100 mg, preferably 30 mg to 60 mg per day, may be used for patients with lower grades of liver disease. Administration at these doses is preferable for benzothiozepines, varapamil, nifedipine and felodipine. The dosage used will however depend upon the nature of the drug and the dosage at which systemic vasodilation occurs. As herein above described the dosage used in accordance with the invention is less than that required to produce a significant effect on the heart or peripheral circulation. We have found that as liver disease progresses lower doses are required with a specific drug, This is believed to be due to the reduced efficiency of the liver in removing the drug as disease progresses so that lower doses are required for a selective effect on the hepatic arterial inflow.

According to a further aspect of the present invention there is provided a pharmaceutical composition suitable for the treatment of liver disease and like indications which composition includes a daily dosage vasodilating agent in an amount less than the oral daily dosage required to produce a significant effect on the heart or peripheral circulation whereby said vasodilating agent selectively increases the supply of oxygenated blood to the liver by increasing hepatic arterial in-flow.

The vasodilating agent may include a calcium blocker, e.g. a thiazepine derivative, preferably a benzothiazepine derivative, nifedipine, felodipine, verapamil or nitroglycerine. Other vasodilators may be used indirectly.

The pharmaceutical composition may be utilised in the treatment of various diseases of the liver such as cirrhosis of a liver, toxic and medicamentary liver damage or liver parenchymic disorders and related diseases such as IO hepatitis including chromic active hepatitis.

The pharmaceutical composition suitable for the treatment of liver disease and like indications may be in the form of a unit daily dosage comprising an amount of vasodilating agent less than required to produce a significant effect on the heart or peripheral circulation. The dosage of preferred vasodilation is approximately 2.5 mg to 60 mg, preferably 10 mg to 60 mg per day vasodilator or its non-toxic acid-addition salt, and a pharmaceutically acceptable diluent or carrier therefor. A dosage at the low level of the range may be used in patients with higher grades of liver disease.

The pharmaceutically acceptable diluent or carrier may be of any suitable type. The pharmaceutically acceptable diluent or carrier may be a pharmaceutical organic or inorganic carrier material suitable for enteral, or oral administration.

The composition is formulated so as to allow suitable oral administration to the patient. The oral route is used as the active ingredient is able to reach the liver directly, that is through the portal vein.

Oral administration by the use of tablets, capsules, powders or in liquid form such as suspensions, solutions, emulsions or syrups is particularly advantageous. When formed into tablets, conventional excipients (e.g, sodium citrate, lactose, microcrystalline cellulose, starch, etc.), lubricating agents (e.g. anhydrous silicic acid, hydrozed castor oil, magnesium stearate, sodium lauryl sulfate, talc, etc.) and binding agents (e.g. starch paste glucose, lactose, gum acacia, gelatin, mannitol, magnesium trsilicate, talc, etc.) can be used.

When administered as liquids, conventional liquid carriers can be employed. In the case of solid preparations, each unit dosage form of the active ingredient can contain from about 5 to about 95% of the same by weight of the entire composition with the remainder comprising conventional pharmaceutical carriers. When the therapeutic agent is used as aqueous solution, i.e, injection, the solution may contain about 0.05 to about 0.5% of the same by weight of the entire solution.

Preferably the composition may be of the sustained release type, for example to allow for a once-daily administration. A suitable slow release formulation may be achieved for example when the active ingredient is bound to a suitable polymer. A once daily composition is able to supply sufficient quantity of active ingredient to the patient and may avoid the possibility of toxic shock where multidoses are given on a daily basis to patients suffering liver disease.

Typical examples of vasodilators and the daily dosages used in accordance with the invention we provided below,

| Vasodilator | daily dose |
| --- | --- |
| Debrisoquine | 5 to 20 mg |
| clonidine | 10 to 50 mg |
| doxazosin | 0.5 to 10 mg |
| prazosin | 0.3 to 1 mg |
| labetalol | 10 to 400 mg |
| irbesartan | 2.5 to 50 mg |
| nifedipine | 0.5 to 10 mg |
| bydrallazine | 2.5 to 35 mg |
| verapamil | 2.5 to 30 mg |
| perindopril | 0.2 to 2 mg |
| cilazapril | 0.5 to 2 mg |
| trandolapril | 0.05 to 0.5 mg |
| lisinopril | 0.5 to 8 mg |
| irbesartan | 2.5 to 60 mg |
| amlodipine | 0.05 to 2.5 mg |
| quinapril hydrochloride | 0.2 to 20 mg |
| captopril | 0.2 to 20 mg |
| enalapril maleate | 0.05 to 5 mg |
| fosinopril | 0.05 to 15 mg |
| ramipril | 0.02 to 2 mg |

The present invention will now be more fully described with reference to the accompanying examples. It should be understood, however, that the description following is illustrative only and should not be taken in any way as a restriction on the generality of the invention described above.

EXAMPLE 1

AIM

A pilot study was undertaken to examine the effect on hepatic artery and mesenteric artery flow in anaesthetised dogs when exposed to cumulative doses of diltiazem.

METHODS

Preparation

Greyhounds were used in this pilot study. All dogs were present in the animal house for <1 week prior to surgery, and all were deemed clinically sound. Dogs were given 15 minutes of exercise prior to arriving at the theatre. On arrival, they were clipped on the abdomen, forelimbs and hindquarters, and anaesthesia was induced with sodium pentobarbitone (Nembutal for Injection T) given intravenously to effect. Subjects were intubated and connected to a respirator. Table heating was used to maintain body temperature. An initial infusion of 1 litre of Hartmann's solution was given throughout the surgical procedure, with bicarbonate being administered as required according to blood gas estimation.

The abdomen was opened, and the gastro-duodenal branch of the common hepatic artery was located and ligated. Electromagnetic flow probes were placed on the common hepatic artery and the anterior mesenteric artery. A branch of the spienic vein was exposed and a catheter introduced and advanced into the portal vein. A catheter was also placed in the left hepatic vein using a purse string technique. An indwelling catheter was placed in a branch of the mesenteric vein, in close proximity to another catheter placed in the lumen of the jejunum. The abdomen was then closed and a catheter introduced into the femoral artery.

The subject was then covered with drapes, and the dogs circulation and temperature allowed to stabilise prior to the commencement of the experimental stage.

At the end of the study, the dogs were euthanased with sodium pentobarbitone.

Experimental Procedure

Theophylline was used infused as a marker of liver extraction. A bolus was given (over 15 minutes) at a rate of 3.42 mg/min, then an infusion into the mesenteric vein at a rate of 11 mg/min. After 90 minutes stabilisation, the first dose of diltiazem was given (0.25 mg/kg) into a jejunal lumen. Time was allowed for any changes in blood flow before the next dose was given. Effects on flow reached a plateau by 20 minutes, when the next dose was given. Cumulative doses were given, i.e. 0.25, 0.5, 1.0, 2.0, 4.0 mg/kg. Blood samples were taken throughout the procedure from the portal vein, posterior hepatic vein and arterial line at 20, 40, 60, 80, 90, 100, 110, 120, 130, 140, 150, 160, 170, 180 and 190 minutes, with zero time being the start of the theophylline infusion.

RESULTS 6 dog Studies were performed, as per the summary in Table 1 below.

| Dog | Preparation | Experimental |
|---|---|---|
| Dog 3/92 | Surgery went well | No flow responses |
| Dog 4/92 | Surgery went well | Excellent flow responses to diltiazem |
| Dog 1/93 | Surgery went well | Flow response to diltiazem |
| Dog 2/93 | Surgery went well | Excellent flow responses to diltiazem |
| Dog 3/93 | Surgery unsuccessful | — |
| Dog 4/93 | Surgery OK | Flow responses to diltiazem |

STATISTICAL OBSERVATIONS

Mean flows were obtained in both the hepatic and mesenteric arteries for 10 to 20 minutes prior to diltiazem being given. This was taken as baseline flows, z and all measurements used this as baseline. Maximum flow responses were measured. The results are summarised in the tables 2a and b below and are presented diagrammatically in FIGS. 1–5.

TABLE 2a

| | Common Hepatic Artery | | | | |
|---|---|---|---|---|---|
| Subject | +% CHA 0.25 mg/kg | +% CHA 0.5 mg/kg | +% CHA 1.0 mg/kg | +% CHA 2.0 mg/kg | +% CHA 4.0 mg/kg |
| 4/92 | 112.4 | 121.7 | 123.2 | 134.0 | 119.6 |
| 1/93 | 99.9 | 86.0 | 71.2 | 73.2 | 140.7 |
| 2/93 | 151.5 | 178.7 | 201.3 | 227.6 | 156.0 |
| 4/93 | 104.7 | 110.1 | 112.8 | 112.8 | 93.5 |
| MEAN | 117.1 ± 11.7 | 124.1 ± 19.7 | 127.1 ± 27.2 | 136.9 ± 32.8 | 127.5 ± 13.6 |

EXAMPLE 2

Two sets of experiments were performed. Both were conducted in dogs anaesthetised with barbiturates.

In the first series nitroglycerin was infused into either the portal vein (draining to the liver from the bowel) or to the femoral vein (systemic circulation). When nitroglycerin was given into the portal vein the blood flow through the hepatic artery (ie. a measure of liver blood flow and oxygenation) increased. By contrast when nitroglycerin was given systemically, hepatic blood flow reduced. It can be concluded that hepatic blood flow and liver oxygenation can both be augmented by drugs, but this cannot be achieved by systemic administration of nitroglycerin.

In the second series, diltiazem was administered by a gastric tube into the stomach-effectively orally. The level of blood flow through the hepatic artery increased by up to 50%, and this occurred at very small doses. Thus, increase in liver perfusion may be achieved by small doses of oral diltiazem and this will have a benefit on the diseased liver.

EXAMPLE 3

A third set of experiments was then undertaken in rats after the earlier studies in dogs had shown that low doses of diltiazem increased liver blood flow. The aim of the study was to induce liver disease by administration of carbon tetrachloride ($CCl_4$) and then test the hypothesis that low doses of diltiazem-would improve the functional state of the liver.

METHODS

Male Sprague Dawley rats were used in this study in which liver disease was induced after the method of Proctor and Chatamra (1982). Hepatic enzymes were first induced by addition of sodium phenobarbitone to the drinking water to a concentration of 350 mg/100 ml. All animals were given the phenobarbitone water for 10 weeks; no other water was available to the animals.

Animals randomised for induction of liver disease received $CCl_4$ added to maize oil, and administered orally through a stainless steel gavage tube during carbon dioxide stun. The $CCl_4$ was given for ten weeks as weekly doses commencing after two weeks of enzyme induction with phenobarbitone sodium. The starting dose of $CCl_4$ was 0.5 ml but the dose was then adjusted according to protocol to achieve a weight loss of 6 to 9% over the 3 days after each dose, with weight gain by day 7. Previous studies have shown that over a period of ten weeks, this regimen will produce liver disease with ascites, splenomegaly, reduction of plasma albumin, increase of plasma alanine transaminase, and the histological features of severe liver disease.

For the assessment of the effects of diltiazem, animals were separated into five groups each of 8 rats. Group 1 (normal) received phenobarbitone in the drinking water but no $CCl_4$ or diltiazem. Group 2 (control) received $CCl_4$ but no diltiazem. Groups 3, 4 and 5 received respectively 0.5, 1.0 and 2.0 mg/kg per day of diltiazem added to the drinking water.

The animals were weighed daily for the four days after each dose of $CCl_4$, and sacrificed after 12 weeks, that is, after 10 weeks of $CCl_4$+/−diltiazem, or at the equivalent time in normal animals. At autopsy, the weights of the livers and spleens were recorded, the presence of ascites and the coat condition was noted, and blood samples were taken for measurement of albumin, liver enzymes and blood clotting factors.

The between group differences for each variable were examined using analysis of variance.

RESULTS

Figure 6A:
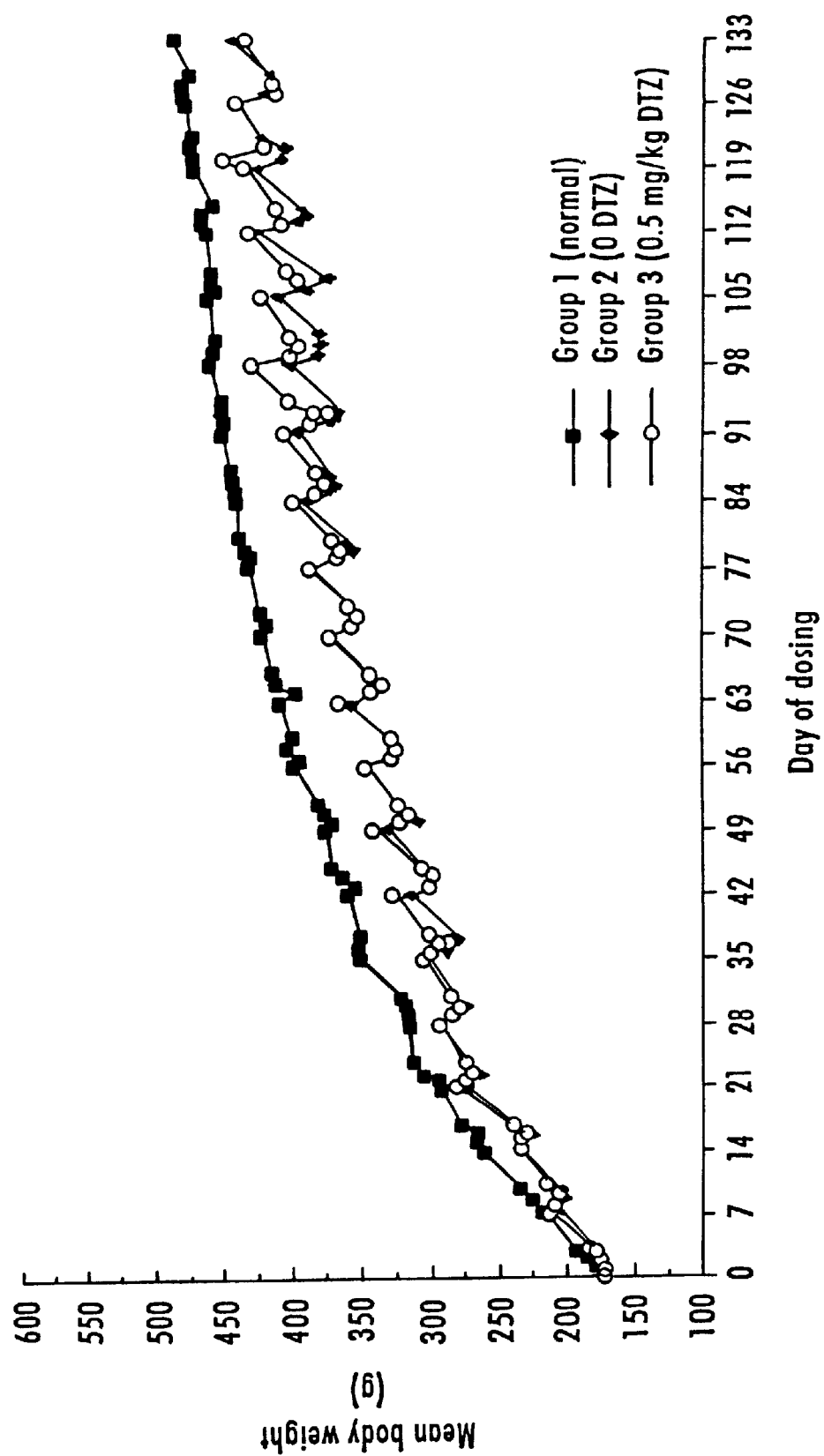
FIGS. 6a, 6b, and 6c are graphs which show body weight profiles during DTZ administration of the results of Example 3.
Figure 6B:
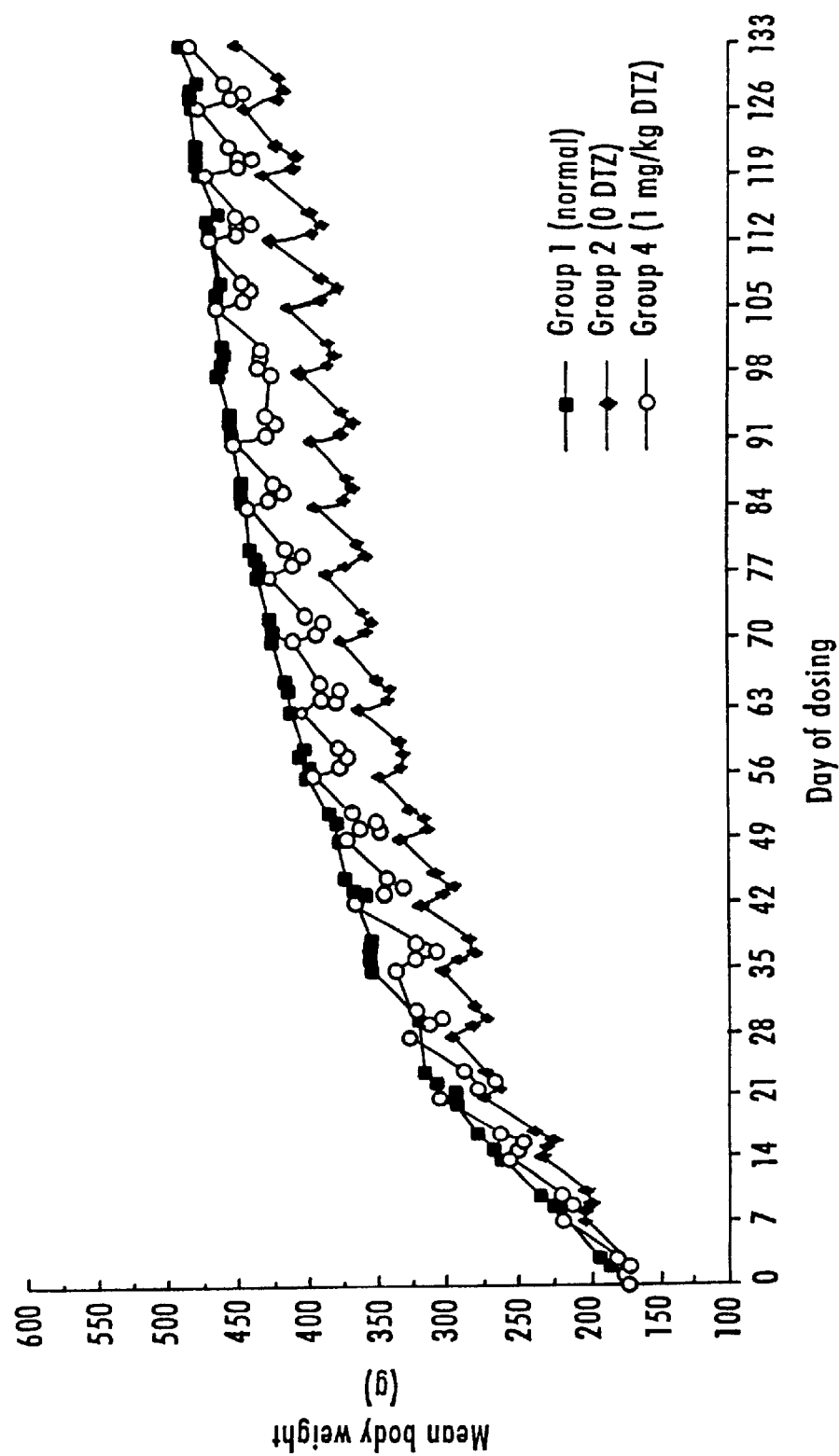
Figure 6C:
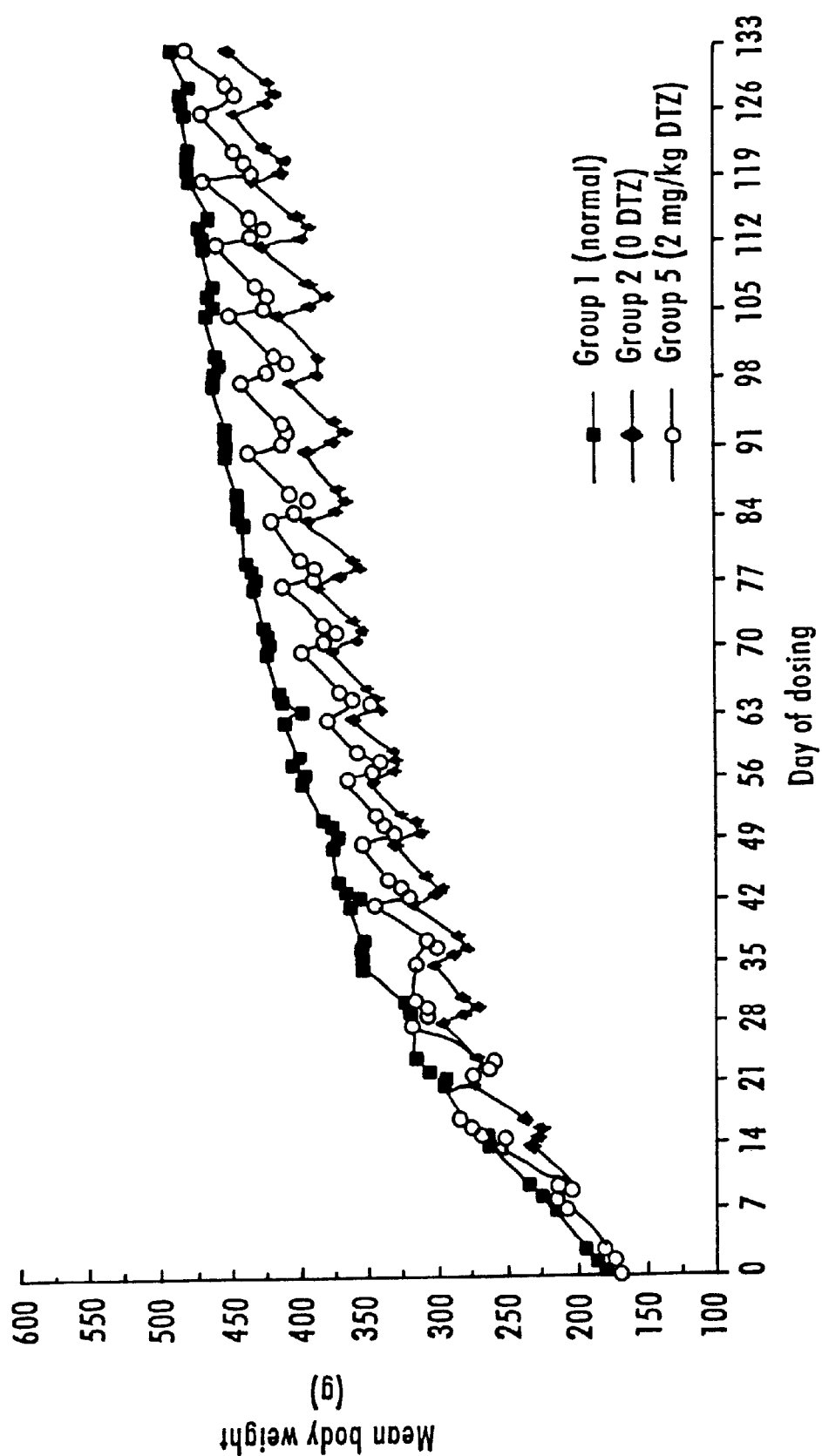

The body weight profiles are shown in FIG. 6a, b, c, which show mean rat body weight profiles during DTZ administration, and $CCl_4$ dosing for induction of cirrhosis in normal, nit DTZ and (6a) 0.5 (6b) 1.0 (6c) 2.0 mg/kg body weight. Group 1 (normal) animals progressively increased in weight from less than 200 grams to about 440 grams body weight over the study period. Group 2 (control) lost weight after each dose of $CCl_4$, and did not gain as much weight as Group 1 being 50 to 60 grams lighter at the end of the study period.

Treatment with 0.5 mg/kg/day of diltiazem (Group 2) appeared to have no significant effect of preventing $CCl_4$-induced weight loss. By contrast, in Group 3 (treated with 1.0 mg/kg/day of diltiazem), there was a transitory loss in weight after each dose of $CCl_4$.

However by the end of the study, body weights were not significantly different from normal (Group 1) but were significantly heavier than those of control animals (Group 2; p<0.05). The effects of 2.0 mg/kg/day (Group 5) appeared to be less than that of 1.0 mg/kg/day.

Autopsy and biochemistry variables are listed in Table 3. In Groups 1 (normal) and 4 (diltiazem, 1.0 mg/kg/day) the liver and spleen appeared normal to inspection, and there was not significant ascites. By contrast Group 2 (control) showed evidence of severe liver disease. The macroscopic changes seen in the control group are supported by the reduction of plasma albumin and clotting factors and increase in plasma alanine transaminase compared with levels in the normal group of animals. Diitiazern afforded significant protection against the development of liver disease as evidenced by the protection against loss of body weight and increase in spleen size and this effect appeared to be greatest at the 1.0 mg/kg/day dose. Those primary indicators are supported by the increased protection against enzyme release. However protection against enzyme release was slightly better at the 2.0 mg/kg/day dose.

Figure 7B:
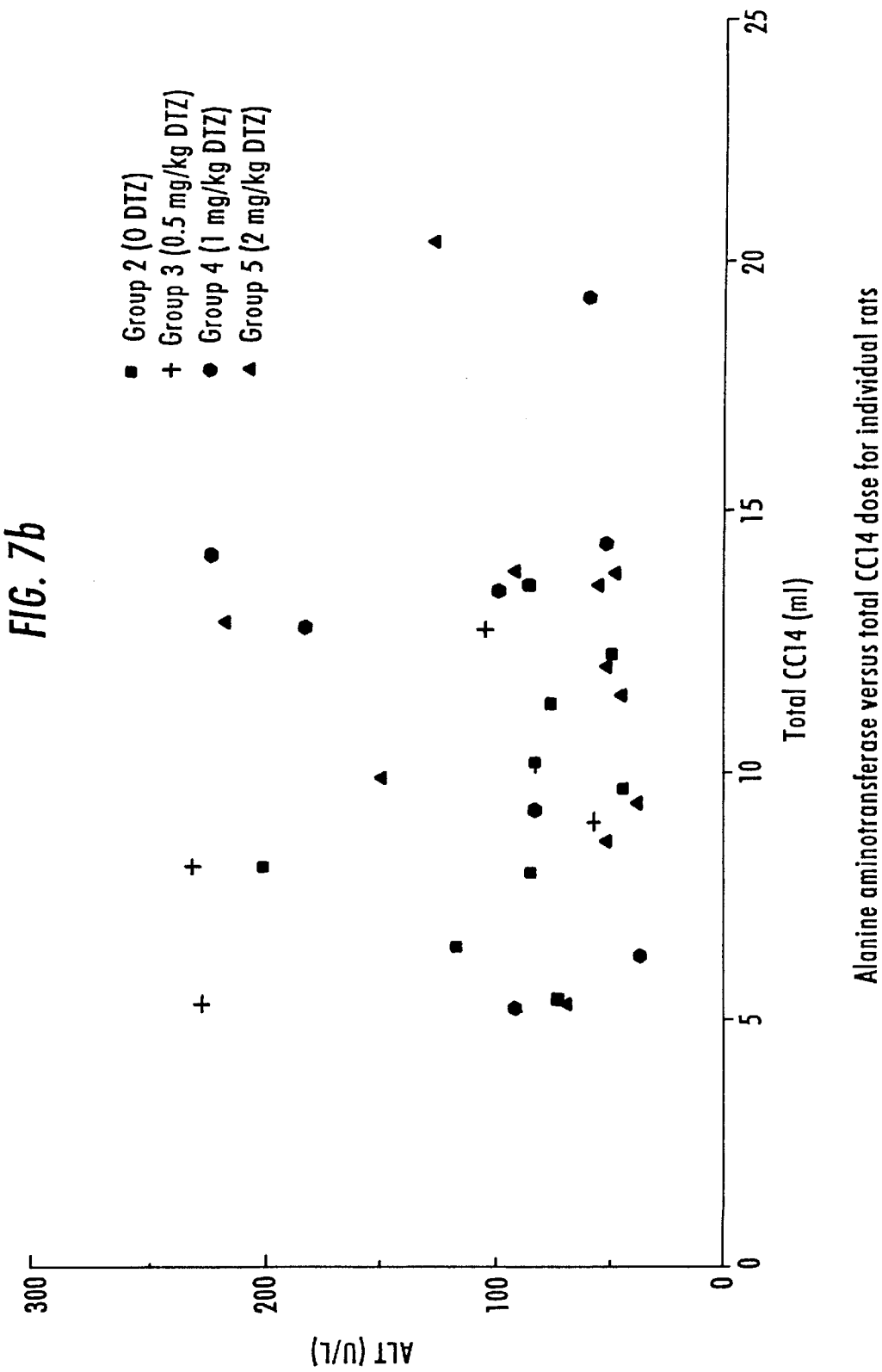

The result reported in Table 3 do, however, somewhat underestimate the protective effects of Dilitiazem against liver disease as the Trial protocol means that healthy animals receive more $CCl_4$ than animals showing signs of liver disease because the weekly dose of $CCl_4$ was titrated against weight loss. The effect of this is illustrated in FIGS. 7a and 7b. FIGS. 7a and b are respectively plots of AST and ALT Enzyme release vs-Total Body load of $CCl_4$.

DISCUSSION AND CONCLUSION

The results of this study in rats show conclusively that low doses of diltiazem significantly prevented the development of liver disease in rats administered with $CCl_4$. Particularly significant is the observation that the greatest effect of diltiazem appeared with a dose of 1.0 mg/kg/day, in respect of body weight and spleen size (an indicator of portal vein congestions), rather than 0.5 or 2.0 mg/kg/day. The previous studies in dogs suggest that the mechanism of action is likely to be an increase in blood flow to the liver, and hence increased oxygenation of the liver. These observations in animals should now be tested in human patients with liver disease. These studies strongly suggest that it will be low doses of Diltiazem which will be effective in treating liver disease in man.

Finally, it is to be understood that various other modifications and/or alterations may be made without departing from the spirit of the present invention as outlined herein.

TABLE 3

Summary of Autopsy and biochemistry variables

| | Group 1 (Normal) | Group 2 (O DTZ) | Group 3 (0.5 mg/ kg DTZ) | Group 4 (1 mg/ kg DTZ) | Group (2 mg/ kg DTZ) |
|---|---|---|---|---|---|
| Liver weight (g per kg body weight) | 34.812 ± 1.353 (n = 10) | 38.695 ± 2.646 (n = 10) | 38.611 ± 2.905 (n = 5) | 40.270 ± 2.488 (n = 9) | 36.947 ± 2.115 (n = 11) |
| Spleen weight (g per kg body weight) | 1.560 ± 0.139 (n = 10) | 3.547 ± 0.374 (n = 10) | 3.096 ± 0.388 (n = 5) | 2.629 ± 0.515 (n = 9) | 2.460 ± 0.230 (n = 11) |
| Albumin (g/L) | 28.44 ± 0.747 (n = 9) | 25.667 ± 1.080 (n = 9) | 29.000 ± 1.484 (n = 5) | 23.875 ± 1.302 (n = 8) | 26.727 ± 0.740 (n = 11) |
| ALT (U/L) | 51.780 ± 4.103 (n = 9) | 92.56 ± 15.48 (n = 9) | 140.60 ± 36.89 (n = 5) | 103.75 ± 23.15 (n = 8) | 86.55 ± 16.99 (n – 11) |
| AST (U/L) | 96.89 ± 9.82 (n = 9) | 190.22 ± 43.10 (n = 9) | 177.40 ± 42.10 (n = 5) | 178.88 ± 47.10 (n = 8) | 127.55 ± 21.54 (n – 11) |
| PT-INR | 0.880 ± 0.020 (n = 5) | 0.960 ± 0.067 (n = 5) | 0.900 ± 0.000 (n – 3) | 0.933 ± 0.042 (n = 6) | 0.920 ± 0.200 (n = 5) |
| APTT (secs) | 24.14 ± 4.39 (n = 5) | 25.18 ± 9.15 (n = 5) | 19.27 ± 1.77 (n – 3 | 18.87 ± 1.35 (n = 6) | 28.02 ± 5.07 (n = 5) |
| Ascites | (n = 0) | (n = 2) | (n = 0) | (n = 1) | (=0) |

ALT Alanine aminotransferase versus total $CCl_4$ dose for individual rats
AST Aspartate aminotransferase versus total $CCl_4$ dose for individual rats
PT Prothrombin Time - International Normalized Ratio
APTT Activated partial thromboplastin time

EXAMPLE 4

Phase I Clinical Studies of Low-Dose Diltiazem in Patients with Liver Disease

Two studies have been commissioned to test the hypothesis that low dose diltiazem may be effective in the management of patients with chronic liver disease. As at January 1996, the first, undertaken in patients with chronic hepatitis (hepatitis C) has been completed and shows a highly significant response in two thirds of patients after just 2 weeks of treatment. This compares favourably with a 30% response rate after 12 weeks treatment with interferon. The result after diltiazem is even more significant in that all patients were refractory to treatment with interferon. A second study in patients with chronic cirrhosis of the liver is on going. However, results in the first two patients indicate that diltiazem administered as 50 mg per day in the 24 hour release formulation is increasing the hepatic clearance of antipyrine, a marker dye of hepatic function.

Study Details a) Chronic Hepatitis

The study of the effects of low-dose diltiazem in chronic hepatitis was undertaken in 24 patients with chronic viral hepatitis (hepatitis C) who had not responded to treatment with interferon, and who had stable, but elevated blood levels of the liver enzyme alanine aminotransferase (ALT) and other enzymes. The study was undertaken at the Alfred Hospital, Melbourne, Australia and had the approval of the Ethics Review Committee at that hospital. Each patient entering the study underwent a run-in phase of two weeks followed by four periods each of two weeks. Diltiazem was administered in incremental doses of 12.5, 25, 50 and 100 mg per day in each of the two week periods. The formulation of diltiazem was Cardizem CD granules reformulated in the respective doses thereby giving low dose, but 24 hour release of the drug. Blood samples for measurement of serum ALT and other hepatic enzymes were taken twice during the run-in period, and then at the end of each incremental dose period. A final measurement of ALT was made at two weeks after completing the study.

A full report is not yet available as at January 1996, but the main results may be summarised as follows. Twenty-four patients entered the study, and 19 completed it. Five patients withdrew because of symptoms of hepatitis and social pressure unrelated to diltiazem. Reasons cited included headache, and impotence during the placebo run-in phase.

Four patients had a modest rise in ALT and two had no significant change. Thirteen had a fall in ALT which appeared to be greatest after the 50 and 100 mg doses. Six patients had a fall in ALT greater than 20%, and this appeared to be greatest after the 50 mg dose, although the response after 25 mg was almost as great. These data approximate to a halving of the evaluation of ALT after just 2 weeks of treatment.

TABLE 4

| | | | Mean change in responders | | |
|---|---|---|---|---|---|
| Time | Dose | n | Mean pre ALT level* | Mean ALT at time | p |
| 4 weeks | 12.5 | 13 | 147.1 | 124.8 | 0.002 |
| 6 weeks | 25 | 14 | 141.3 | 112.9 | 0.003 |
| 8 weeks | 50 | 13 | 146.3 | 109.8 | 0.001 |
| 10 weeks | 100 | 11 | 159.5 | 105.3 | 0.008 |
| post (average) | | | 159.6 | 123.6 | 0.003 |

*Upper limit of normal for ALT is 40 lu/ml

Data from patients who experienced more than 20% fall in ALT are shown in Table 5

| Time | Dose | n | Mean pre ALT level* | Mean ALT at time | p |
|---|---|---|---|---|---|
| 4 weeks | 12.5 | 3 | 170.3 | 126.7 | 0.002 |
| 6 weeks | 25 | 6 | 157.1 | 104.5 | 0.003 |
| 8 weeks | 50 | 6 | 142.1 | 95.6 | 0.001 |
| 10 weeks | 100 | 6 | 153.1 | 105.0 | 0.008 |
| post (average) | | 7 | 160.0 | 106.3 | 0.003 |

The overall data are consistent with an adjunctive and therapeutic effect, and match the effects of low-dose diltiazem seen in animals. The study can not show whether a higher response rate or greater therapeutic effect may be achieved after longer periods of therapy. However, the results need to be compared with those from studies of interferon, a curative therapy, where the time to response is reported to be twelve weeks.

On this basis, the data showing incremental effects throughout the study could reflect a response to aggregate time of exposure, rather than necessary attributing the increments in effect throughout the study to the increments in dose.

It is also interesting to note that ALT did not appear to rise immediately after stopping the diltiazem. This is consistent with reoxygenation by hepatic artery dilation thereby permitting a healing effect, rather than interfering directly with the disease process. There was no evidence that 100 mg was more effective than 50 mg. The rise of enzymes in four patients indicates that the dose of the drug should be kept as low as possible.

Patients also reported that they felt better while taking the drug. Several individuals reported less tiredness and headache, and more energy.

b) Cirrhosis of the Liver

This study is logistically difficult to do and is incomplete. Ten patients with chronic but stable cirrhosis of the liver are to be recruited and each will receive 50 mg of diltiazem formulated from the 24 hour release Cardizem CD granules. An antipyrine clearance study will be performed in each patient on recruitment, after the first dose of treatment and then again after two weeks of treatment. If possible measurement of propranolol clearance will be performed at the same time. The purpose of the antipyrine clearance is to measure hepatic function in terms of the ability of the liver to excrete substances into the bile. The purpose of the propranolol clearance is to measure the capacity of the cytochrome p450 system, which is critical for oxidation and hydroxylation processes with the liver. A clearance study involves intravenous injection of a dye or marker (in this case antipyrine or radio-labelled propranolol), followed by repeated blood tests for up to 12 hours. The decay in blood levels of the marker permits measurement of the clearance rate of the dye from the body, and in this case by the liver.

As at January 1996, two patients have completed the clearance study, and both show an increase in the clearance of antipyrine. The first patient increased antipyrine clearance from 468.2 units before treatment, to 494 units after the first dose, and 730.4 units after 2 weeks treatment. This represents a 56% increase in antipyrine clearance in a patient with severe disease. The second patient with more severe disease, had a lesser but significant increase.

EXAMPLE 5

Figure 8:
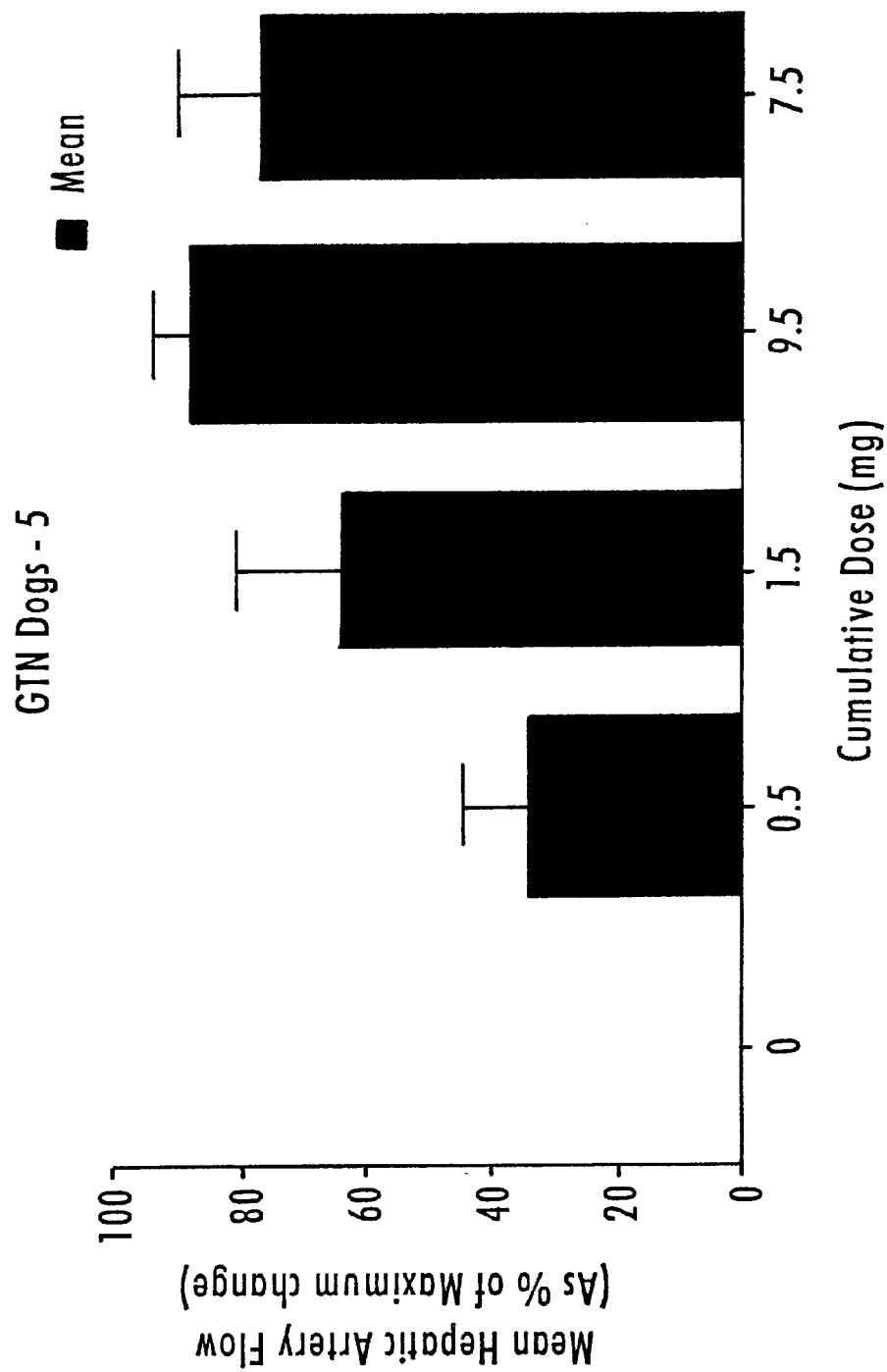
FIG. 8 is a graph of the mean hepatic artery flow during administration of nitroglycerine.

Five greyhounds were used in a pilot study to examine administration of nitroglycerine. Using the procedure described in Example 1 the greyhounds were prepared and Theophylline infused as a marker of liver extraction, Mean hepatic artery flows were measured and maximum flow responses were measured. The results are shown in FIG. 8 and nitroglycerine was found to provide a similar level of improvement in arterial flow to that found using diltiazem.

It should be noted that while the hepatic artery flow is progressively increased with cummulative doses of 0.5, 1.5 and 3.5 the flow is significantly decreased on increasing the cummulative dose to 7.5 mg. This reduction is due to systemic arterial pressure fall. The systemic arterial pressure fall is exacerbated at higher doses so that the advantage of improved arterial inflow observed at low doses is lost.

EXAMPLE 6

Experiments were performed on Wistar rats aged between 4 and 5 weeks postnatal. Animals were anaesthetized with ether anaesthetic and killed by cervical dislocation. For all experiments the hepatic artery proper was dissected from the point where it separated from the coeliac artery to the point where its branches enter the liver parenchyma.

In vitro experiments

After dissection, the hepatic arterial tree was immobilized by pinning the adjacent mesentery in a 1 ml bath whose base was covered in a thin layer of silicone (Sylgard, Dow Corning Corporation, Midland U.S.A.). Preparations were superfused with Krebs' solution (mM): NaCl 119.8, KCl 5.0, $CaCl_2 \cdot 6H_2O$ 2.5, $MgCl_2 \cdot 6H_2$) 2.0, $NaH_2PO4 \cdot H_2O$ 1.0, $NaHCO_3$ 25 and D-glucose 27.7, gassed with 5% $CO_2$/95% $O_2$, at 34° C. in the tissue bath. Hyoscine hydrochloride ($10^{-6}$M) and capsaicin ($10^{-6}$M) were added to the Krebs' solution at all times to prevent the effects of cholinergic and sensory nerves respectively. Preparations were allowed to equilibrate for 45 min prior to transmural stimulation (10 Hz, 10 s, 60 V, 0.1 mscc pulse duration) every 20 min via platinum electrodes plased 5 mm apart on opposite sides of the preparation. Preliminary experiments were performed to determine the minimal stimulation parameters, with regard to frequency and duration, that would produce a response of reasonable size that could be blocked by tetrodotoxin. The artery was visualized using video microscopy and the vessel diameter was continually monitored (DIAMTRAK). Data were collected and measured on a Maclab Chart Recorder (ADInstruments U.S.A.). All experiments were performed on second or third order branches of the hepatic artery within the mesentery (mean resting diameter, 78.52±2.23 $\mu$m, n=113). These diameters would be larger than the actual vessel diameter in vivo due to the pinning of the surrounding presentery, however vessels were not occluded and blood movement was always observed during nerve stimulation.

Control experiments were performed to determine the time period over which consistent responses could be achieved. The magnitude of the vasoconstrictor response to nerve stimulation was expressed as a percentage of the resting vessel diameter, This was done in order to standardize nerve-mediated responses in vessels of different resting diameter. Prior to the addition of any drug, the average of two to three nerve-mediated responses in control Krebs' was calculated. For each drug or specific drug concentration, at least two responses were averaged once a consistent response appeared. This meant that drugs were perfused for at least 20 min, the time between sequential nerve stimuli. The response in the drug solution was expressed as a percentage of the control response. Experimental values are given as the mean±s.e. mean of results from at least four preparations, where each preparation was obtained from a different animal. All results were obtained with the appropriate drug present in solution except for the irreversible $\alpha$-adrenergic blocker benextramine, whose effect was determined after a washout period of 20 min to avoid any non-specific actions Statistical significance was tested using a paired two tailed Students t-test and a P value of <0.05 was taken as significant. Concentration response curves were constructed using Axograph (Axon Instruments) and a Hills $X^2$ equation to fit the curves. The half maximal inhibitory concentration ($IC_{50}$) was calculated directly from the curves, Drugs and Solutions The following drugs were used: tetrodotoxin, (−)byoscine (scopolamine) hydrochloride, guanethidine sulphate (GE), benextramine tetrachloride, prazosin hydrochloride U.S.A. $\alpha,\beta$-mATP, pyridoxal phosphate-6-azophenyl 2'–4'– disulphonic acid tetrasodium (PPADS).

All drugs were made up as at least 100 x stocks in water except for capsaicin (100% ethanol), prazosin (20% v/v methanol) and 5-methyl-urapidil and WB4101 (0.1 m hydrochloric acid). Dilutions of all stocks were made in Krebs' for final concentrations. Diluents were tested at appropriate concentrations. Appropriate precautions were taken for light-sensitive drugs, including illuminating the preparations with only long wavelength light (>610 nm).

Figure 9A:
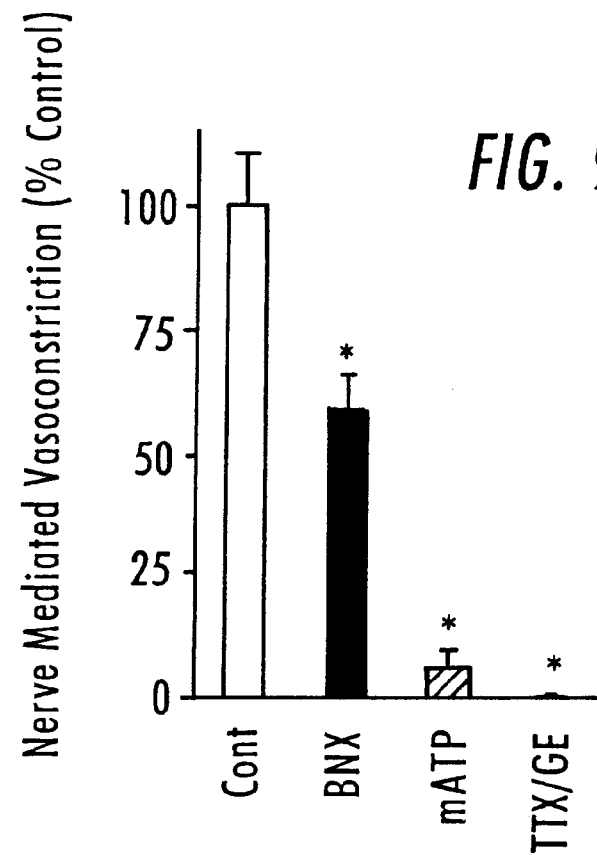
FIG. 9 is a graph showing the vasodilating effect of PPADS, tetrodotoxin, benextramine and guanethidine on the hepatic artery.
Figure 9B:
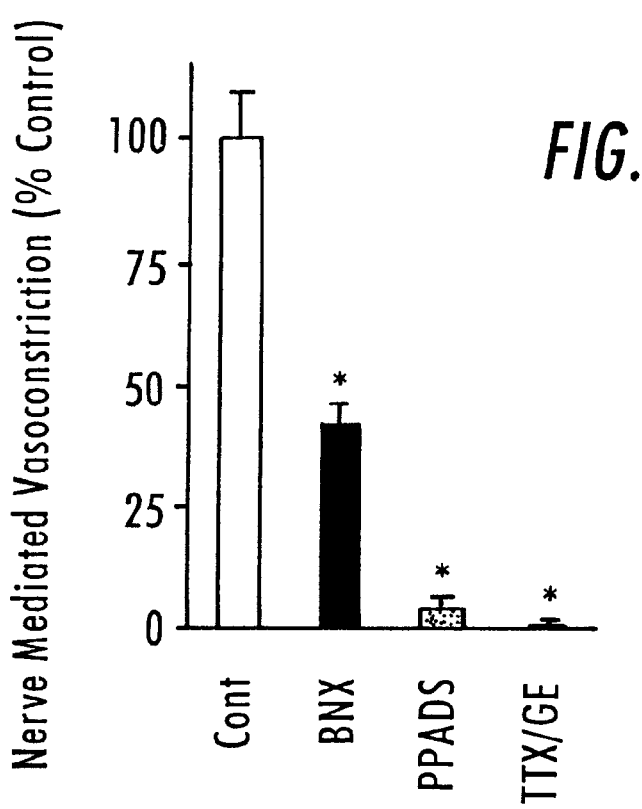

FIG. 9$a$ and 9$b$ show the effects of the cumulative consecutive application of (a) benextramine (BNX, $10^{-3}$M) and $\alpha,\beta$-mATP (mATP, $3\times10^{-6}$M) or (b) BNX and PPAADS ($10^{-5}$M) on the nerve-mediated contractile response of arteries in the rat hepatic mesentery. Tetrodotoxin (TTX, $10^{-6}$M) and/or guanethidine (GE, 5 z $10^{-6}$M) abolished the small residual contraction. Columns represent the means±s.e. mean of at least 4 preparations. Results are expressed as % of the contractile response in control Krebs solution (Cont). Control response in (a) was 20.78±2.64% of resting vessel diameter, n-7 and in (b) was 17.92±1.68%m n-8.

The symbol "*" in FIG. 9($a$) and 9($b$) indicates a significant difference from the control (P>0.05).

I claim:

1. A method for the treatment of liver disease selected from the group consisting of cirrhosis of the liver, toxic and medicamentary liver damage, a liver-parenchymic disorder or hepatitis, comprising administering orally to a human or animal subject in need thereof a low dose of a vasodilating agent whereby said vasodilating agent selectively increases the supply of oxygenated blood to the liver by increasing hepatic arterial inflow with no significant fall of systemic arterial blood pressure.

2. A method in accordance with claim 1 wherein the vasodilator is selected from the group consisting of nifedipine, felodipine, verapamil and nitroglycerine.

3. A method in accordance with claim 2 wherein the vasodllating agent is administered in an amount of approximately 2.5 to 60 mg per day.

4. A method according to claim 1 wherein the vasodilator is administered in the form of a sustained release fonnulation once daily.

5. A method according to claim 1 wherein the vasodilator is selected from the group consisting of debrisoquine, clonidine, doxazosin, pazosin, labetalol, irbesartan, lydrallazine, minoxidil amladipine.

6. A method according to claim 1, wherein the vasodilating agent is administered in a slow release formulation.

* * * * *